United States Patent
El-Say et al.

(10) Patent No.: US 10,653,634 B1
(45) Date of Patent: May 19, 2020

(54) POLYMERIC NANOPARTICULATE FORMULATION TO ENHANCE THE ORAL BIOAVAILABILITY OF DAPOXETINE

(71) Applicants: King Abdulaziz University, Jeddah (SA); VIRGINIA COMMONWEALTH UNIVERSITY, Richmond, VA (US)

(72) Inventors: Khalid M. El-Say, Jeddah (SA); Osama A. A. Ahmed, Jeddah (SA); Amir I. Mohamed, Jeddah (SA); Abdelsattar M. Omar, Jeddah (SA); Martin K. Safo, Richmond, VA (US)

(73) Assignees: King Abdulaziz University, Jeddah (SA); Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/719,248

(22) Filed: Dec. 18, 2019

(51) Int. Cl.
| | |
|---|---|
| *A61K 9/51* | (2006.01) |
| *A61K 31/138* | (2006.01) |
| *A61P 15/12* | (2006.01) |
| *A61K 9/19* | (2006.01) |

(52) U.S. Cl.
CPC .............. *A61K 9/5169* (2013.01); *A61K 9/19* (2013.01); *A61K 9/5123* (2013.01); *A61K 9/5192* (2013.01); *A61K 31/138* (2013.01); *A61P 15/12* (2018.01)

(58) Field of Classification Search
CPC ...... A61K 9/5169; A61K 9/5123; A61K 9/19; A61K 31/138; A61K 9/5192; A61P 15/12
See application file for complete search history.

(56) References Cited

FOREIGN PATENT DOCUMENTS

EP        2698147 A1 *  2/2014  ......... A61K 31/4985

OTHER PUBLICATIONS

Abourehab et al. (International Journal of Nanomedicine, 2018:13 3679-3687) (Year: 2018).*
Fahmy and Aljaeid (Int. J. Pharmacol., 14 (7): 945-951, 2018) (Year: 2018).*
Hashem et al. (International Journal of Nanomedicine 2015:10 4059-4069) (Year: 2015).*

* cited by examiner

*Primary Examiner* — Robert S Cabral
(74) *Attorney, Agent, or Firm* — W & C IP (57) ABSTRACT

Dapoxetine nanoparticles comprising zein and alpha lipoic acid (ALA) are provided. When present in zein-ALA loaded nanoparticles, dapoxetine exhibits increased bioavailability (compared to conventional formulations) when administered to subjects for the prevention or treatment of premature ejaculation (PE). Thus, lower doses are administered, and side effects are attenuated or eliminated.

13 Claims, 8 Drawing Sheets

POLYMERIC NANOPARTICULATE FORMULATION TO ENHANCE THE ORAL BIOAVAILABILITY OF DAPOXETINE

BACKGROUND OF THE INVENTION

Field of the Invention

The invention generally relates to dapoxetine nanoparticles comprising zein and alpha lipoic acid (ALA). In particular, the invention provides zein-ALA loaded dapoxetine nanoparticles which exhibit increased bioavailability compared to conventional formulations, e.g. when administered for the treatment of premature ejaculation (PE).

Description of Related Art

The Global Study of Sexual Attitudes and Behaviors (GSSAB) has reported the Premature ejaculation (PE) to be approximately 30% across all age groups.[1-3] PE is associated with serotonin neurotransmission imbalances, which is usually not related to other chronic disorders.[4]

Dapoxetine (DPX), with an antidepressant property, is the first serotonin transporter inhibitor successfully used for the treatment of PE.[5-7] DPX increases the action of serotonin at the postsynaptic cleft. The fast-acting effect and rapid elimination of DPX make it a good candidate for the treatment of PE, but not as an antidepressant. The efficacy and safety of DPX in the treatment of PE were confirmed in 2011 and granted marketing authorization for 30 mg and 60 mg film-coated tablets in the European Union.[8] Nonetheless, DPX suffers from low bioavailability with large variability 15-76% (mean 42%) after oral administration. The peak plasma concentration of DPX after oral administration is reached within 60-80 min and is dose-related.[9,10] Nausea, dizziness, headache, insomnia, fatigue, and nasopharyngitis represent the most commonly treatment-related adverse effects of DPX.[11] These deleterious side effects are dose-dependent and largely synchronized with the pharmacokinetic profile of DPX.[7]

It would be beneficial to have available improved DPX formulations with increased bioavailability after oral administration, so that the therapeutic dose could be decreased, thereby lowering the incidence of adverse side effects.

SUMMARY OF THE INVENTION

Provided herein are nanoparticles (NPs) comprising dapoxetine (DPX), zein and alpha lipoic acid (ALA) i.e. DPX "loaded" zein-ALA NPs. When administered e.g. for the treatment of premature ejaculation (PE), the nanoparticles provide increased absorption and oral bioavailability of the DPX. For example, some DPX-loaded NP formulations showed a 194% improved relative bioavailability when compared to a prior art DPX tablet, permeability and absorption via mucosal membranes was increased. Therefore, when DPX is administered using the NPs, the dose of DPX that is needed to successfully treat PE is lowered and the number and/or severity of side effects are thus lessened.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide nanoparticles comprising dapoxetine, zein and alpha-lipoic acid (ALA). In some aspects, the nanoparticles range in size from 145 to 210 nm. In some aspects, the nanoparticles have a zeta potential of 20 to 25 mvolts. In further aspects, in the nanoparticles, the dapoxetine is present in a weight percentage of 3 to 35; the zein is present in a weight percentage of 50 to 70, and the ALA is present in a weight percentage of 3 to 10. The invention also provides pharmaceutical compositions comprising the nanoparticles.

The invention also provides a method of treating or preventing premature ejaculation (PE) in a subject in need thereof, comprising administering to the subject a therapeutically effective dose of a pharmaceutical composition comprising the nanoparticles. In some aspects, the therapeutically effective dose of DPX in a dose of nanoparticles is less than 30 mg.

Also provided is a method of making nanoparticles comprising dapoxetine, zein and alpha-lipoic acid (ALA). The method comprises: combining a DPX-zein-ALA organic solution with an aqueous polyvinyl alcohol (PVA) solution to yield a colloidal dispersion of the nanoparticles. In some aspects, the organic solution is a methanolic solution. In other aspects, the method further comprises steps of removing organic solvent from the colloidal dispersion; and removing water from the colloidal dispersion. In some aspects, the step of removing water is performed by lyophilization. In additional aspects, the method comprises one or more steps of washing, centrifugation and/or dialysis. In further aspects, the step of combining is performed by stirring at 1000 rpm or greater.

DETAILED DESCRIPTION

The present disclosure provides new nano-particulate (NP) formulations of DPX which exhibit improved bioavailability of the drug. The doses of the new formulations that are required to achieve effective treatment of PE are lower than prior art formulations. Therefore, administration of the 
new formulations to a subject result in fewer unwanted side effects and/or lessens the severity of unwanted side effects.

In the new formulations, DPX is encapsulated in zein and the antioxidant alpha-lipoic acid (ALA). As described herein, mathematical experimental designs were utilized to design formulation parameters for the preparation of the new DPX-zein-ALA NPs.

Definitions

Dapoxetine (DPX) as used herein generally refers to (S)-dapoxetine, especially (S)-dapoxetine-HCl having IUPAC name (1S)—N,N-dimethyl-3-naphthalen-1-yloxy-1-phenylpropan-1-amine, generally as the hydrochloride.

Zein refers to a class of prolamine protein found in maize (corn). It is usually manufactured as a powder from corn gluten meal. Pure zein is advantageously clear, odorless, tasteless, hard, water-insoluble (hydrophobic), and edible, making it suitable for inclusion in pharmaceutical preparations.

ALA is an antioxidant also known as Acetate Replacing Factor, Biletan, Lipoicin, Thioctan, and other names. ALA is a naturally occurring fatty acid that can be found in many foods such as yeast, spinach, broccoli, potatoes, and organ meats such as liver or kidney. It is thus safe for human consumption and for inclusion in pharmaceutical preparations.

"ALA in zein" refers to a mixture of ALA and zein in proportions such that the percentage of ALA in a mixture of "ALA in Zein" ranges from e.g. about 10-25% (such as about 10, 11, 12, 13, 14, 15, 16, 17, 18, 19, 20, 21, 22, 23, 24 or 25%) and is usually about 15-20%, such as about 15, 16, 17, 18, 19 or 20% ALA. Preferably, the "ALA in zein" comprises about 15% ALA as a percentage of the total weight of the mixture. A preferred combination is, for example, 15 mg ALA and 85 mg Zein. ALA and Zein is considered as the polymeric matrix that forms the nanoparticles described herein.

Poly(vinyl alcohol) (PVOH, PVA, or PVA1) is a water-soluble synthetic polymer having the (idealized) formula $[CH_2CH(OH)]n$. It is colorless (white), odorless and biocompatible.

As used herein, "nanoparticles" are particles between about 1 and 500 nanometers (nm) in size (inclusive) that are typically surrounded by an interfacial layer. "Size" generally refers to the particle diameter of an NP and/or the average particle diameter of a plurality of NPs in a preparation. The interfacial layer typically comprises ions, inorganic and organic molecules. In nanotechnology, a particle is defined as a small object that behaves as a whole unit with respect to its transport and properties.

Zeta potential (ζ) refers to the electrokinetic potential of a particle in colloidal dispersions. The usual units are volts (V) or millivolts (mV). From a theoretical viewpoint, the zeta potential is the electric potential in the interfacial double layer (DL) at the location of the slipping plane relative to a point in the bulk fluid away from the interface. In other words, zeta potential is the potential difference between the dispersion medium and the stationary layer of fluid attached to the dispersed nanoparticle.

In some aspects, DPX is "encapsulated" by a zein/ALA mixture. "Encapsulate" as used herein generally refers to the DPX being substantially enclosed or contained within the zein/ALA NP matrix. A portion or all of the DPX may be present in an inner core of zein/ALA matrix. However, generally those of skill in the art will recognize that a portion of the DPX may also be mixed in with the zein/ALA coating.

The individual nanoparticles disclosed herein generally comprise DPX, zein and ALA. In some aspects, the DPX is DPX-HCl, or DPX base may also be present.

The amount of each component of the NPs may vary from particle to particle, or from preparation to preparation, but in general the amount of DPX is in the range of from about 15 to about 60 mg of DPX per 150 mg of NPs. Those of skill in the art will recognize that, when administered, the NPs will be present in a formulation such as within a capsule, in a tablet, etc. as described elsewhere herein, and the final amount that is administered is determined by 1) the amount of DPX per NP (or per mg of NPs) and 2) the total amount or weight of NPs that are in a single dose of a formulation.

Typically, the weight percentage of "ALA in zein" in the NPs is from about 10 to 30%, and is usually about 15 to 25, such as about 15, 20 or 25. However, the experimental data presented herein showed that lower percentages are advantageous, resulting in smaller particle sizes and higher zeta potentials. Thus, the weight percentages may be lowered, e.g. to from about 5 to 15, such as about 5, 6, 7, 8, 9, 19, 11, 12, 13, 14, or 15, including all integers in between those values, to the closest 0.5 decimal place, e.g. about 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5 or 15.0. It is noted that 15-25% of ALA used was the % of ALA in ALA-zein mixtures, but the final NPs contain, in addition to the ALA-zein mixture, DPX and PVA.

In the final nanoparticle preparations, e.g. after lyophilization DPX is present in a weight percentage of about 10 to 40 including all integers from 10 to 40, inclusive, such as 10, 11, 12, 13, 14, etc up to about 35, 36, 37, 38, 39 and 40; the zein is present in a weight percentage of from about 50 to 70 e.g. about 50, 55, 60, 65, or 70% including all integers in between such as about 50, 51, 52 . . . up to about 67, 69, 70; and the ALA is present in a weight percentage of 10 to 20, e.g. about 10, 11, 12, 13, 14, 15, 16, 17, 18, 19 or 20%.

Other components may also be present in the NPs, for example, ions such as anions or cations associated with charged, hydrophilic or hydrophobic groups of the DPX, zein and/or ALA; residual cryoprotectants e.g. sugars such as mannitol; residual PVA, residual $H_2O$ molecules, etc. Also, void spaces may be present in the NPs. In general, such extraneous components are present in very low amounts, such as less than about 5% wt/wt, e.g. less than about 5, 4, 3, 2, or 1% wt/wt of the final product (dried NPs ready for packaging into dosage forms acceptable for administration).

The average size of the NPs can be varied from preparation to preparation, and some variation (e.g. about ±1-5%) occurs between particles in a single preparation. The average size is generally from about 130 to about 200 nm, such as from about 140 to about 180 nm, e.g. from about 145 to about 175 nm. In some aspects, the average size is about 145, 146, 147, 148, 149, 150, 151, 152, 152, 154, 155, 160, 165, 170 or 175 nm, including all integers in between those values, to the closest 0.1 decimal place, e.g. about 148.0, 148.1, 148.2, 148.3, 148.4, 148.5, 148.6, 148.7, 148.8, 148.9, 150.0 and 150.1, 150.2 and so on up to about 175 nm. The prepared 15 formulations showed particle size range from 148.6 to 206.8 while the optimized formulation with the optimal combination gave particle size of about 159 nm. In fact, if desired, the NP particle size can be varied to afford different levels and/or times of release of the DPX.

The ζ potential of the NPs is generally from about 5 to about 25 millivolts (mv), such as from about 0.1 to 25-30 my, e.g. about 0.1. 0.1, 1.0, 5.0, 10.0, 15.0, 20.0.25.0 or 30.0 my, including all integers in between those values, to the closest 0.1 decimal place, e.g. about 0.1, 0.2, 0.3, 0.4, 0.5 . . . and so on up to and including e.g. 10.0, 10.1, 10.2, 10.3, 10.4, 10.5 . . . and so on up to and including e.g. 19.0, 19.5, 19.6, 19.7, 19.8, 19.9 and 20.0 . . . and so on up to and including e.g. 29.5, 29.6, 29.7, 29.8, 29.9 and 30.0, and so on for all integers and decimal fractions thereof, from about 0.1 to about 30. In preferred aspects, the range is from about 0.2 to about 25, or 0.2 to about 20. The prepared 15 formulations described in the Examples showed zeta potential range from 0.2 to 20 while the optimized formulation with the optimal combination gave a zeta potential of about 19 nm.

The DPX initial release pattern of the NPs described herein is excellent, with at least about 20% of the DPX released after 1 hour, and typically at least about 35% or even up to about 40% being released initially, especially for NPs with relatively small sizes. The cumulative release pattern is also excellent. For example, after 24 hours over 85% of the DPX is released, and in many cases, over 90% or even over 95% (e.g. about 96 or 97%) is released from the NPs.

Compositions and Formulations Comprising Nanoparticles

The nanoparticles described herein are generally delivered (administered) as a pharmaceutical composition that includes a carrier, and the present invention encompasses such formulations/compositions. The compositions generally include a plurality of nanoparticles as described herein, the plurality being sufficient to make up a suitable dose (e.g. a single dose) and a pharmacologically suitable (physiologically compatible) carrier, which may be liquid (e.g. aqueous or oil-based) or solid. In some aspects, such compositions are prepared as liquid solutions or suspensions, or as solid forms such as tablets, pills, powders, within capsules (such as gelatin capsules, hydroxypropyl methylcellulose (HPMC) capsules, etc.), nanoparticles embedded in a solid lipid carrier or suspended in a liquid lipid carrier, and the like. Solid forms suitable for solution in, or suspension in, liquids prior to administration are also contemplated, as are emulsified preparations. In some aspects, the nanoparticles, and/or the carriers in which they are delivered, are mixed with inert excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients to provide the composition in a form suitable for administration. The final amount of DPX, zein and/or alpha lipoic acid in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The PDX formulations are generally intended to be short-acting, e.g. for release of the active agent, for example, within about 0.5, 1.0, 1.5, 2.0, 2.5 or 3.0 hours. However, extended or timed-release formulations are also encompassed.

Dosage forms of the compositions are also provided, such as bottles or blister packs comprising single dose tablets or capsules containing the NPs, etc. having a suitable amount of DPX in each dose.

Administration

The DPX nanoparticles and/or formulations thereof are administered in vivo by any suitable route including but not limited to: by injection, by inhalation (e.g. as a mist or spray), orally (e.g. as a pill, capsule, liquid, etc.), etc. In preferred embodiments, the mode of administration is by oral administration of a solid formulation.

When using conventional DPX formulations, the amount of DPX that is administered per dose is generally in the range of from about are generally 30 or 60 mg per dose. Since the present NPs afford greater bioavailability of DPX, the dose may be lower than those of the prior art. Thus, the dose may be lowered, e.g. to about 5 to about 50 mg per dose, such as about 5, 10, 15, 20, 25, 30, 35, 40, 45 or 50 mg per dose.

Methods of Making DPX Loaded Zein-Ala Nanoparticles

Also provided herein are methods of making DPX-loaded zein-ALA encapsulated NPs. The methods generally comprise steps of:

1. combining a DPX-zein-ALA organic solution with an aqueous PVA solution to yield a colloidal NP dispersion; and then
2. removing MeOH from the colloidal NP dispersion; and 3. removing water from the colloidal NP dispersion to yield a dry preparation or composition of NPs.

In some aspects, prior to step 1, the method includes one or both of a) a step of combining PVA and water to yield the aqueous PVA solution, and b) a step of combining DPX, zein and ALA (or combining DPX and "ALA in zein", i.e. the ALA and zein are already combined or premixed) in a suitable organic solvent to yield the DPX-zein-ALA organic solution. Examples of suitable organic solvents include but are not limited to: methanol, ethanol, propanol or mixtures of these. The percentage of "ALA in zein" used to make the organic solution generally ranges from about 10 to about 30, such as about 10, 15, 20, 25 or 30, wt/wt of ALA/zein mixture. Experiments described in the Examples section below showed that lower percentages are advantageous, so that a favorable range may be from about 5 to 15%, such as about 5, 10, or 15%.

The percentage of PVA (wt/vol) in the aqueous PVA solution generally ranges from about 0.1 to about 2.0, such as about 0.5, 1.0, 1.5 or 2.0.

Step 1 is typically performed by mixing or stirring the two solutions together. If stirred, the rate of stirring is generally in the range of from about 500 to 1500 rpm, such as about 500, 600, 700, 800, 900, 1000, 1100, 1200, 1300 1400 or 1500 rpm. In some aspects, higher rates of stirring were found to be advantageous, e.g. at least 1000 rpm e.g. 1200 rpm, to achieve desired results with respect to e.g. smaller NP sizes and increased bioavailability.

In some aspects, step 2 is performed via rotary evaporation. However, other methods known in the art may be used.

In some aspects, the colloidal NP dispersion is e.g. centrifuged and/or washed (such as with deionized water or another suitable solvent) prior to step 3. Such steps serve to remove residual PVA.

In step 3, water is removed, i.e. the preparation is dried. This may be done by any suitable technique, e.g. by lyophilization (freeze drying) or some other form of drying such as gentle heating, evaporation (e.g. under vacuum), etc. If the residual mixture is lyophilized, generally a cryoprotectant is added in an amount sufficient to prevent damage to the particles, e.g. various biocompatible sugars and/or sugar alcohols (mannitol, trehalose, a sucrose and sodium phosphate solution, etc.), various electrolytes, etc. are added.

If lyophilized, the lyophilized composition comprises the NPs as described herein, and possibly residual cryoprotectant, which may or may not be removed prior to administration, to yield a dry preparation of NPs.

Those of skill in the art will recognize that additional techniques may be used in various steps to replace those listed above, and/or in additional purification or separation steps which may be added to the method. For example, additional steps of filtration, dialysis, centrifugation, washing, sizing, etc. of the NPs may be included. Such steps may be used, for example, to dry and/or aid in purifying NPs and/or selecting desired sizes of NPs, etc. prior to packaging and administration.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting example which further illustrates the invention, and is not intended, nor should it be interpreted to, limit the scope of the invention.

Example

Materials and Methods
Materials

DPX was a gift. ALA, zein, polyvinyl alcohol (PVA), acetonitrile and methanol were purchased from Sigma-Aldrich Corporation (St. Louis, Mo., USA).

Experimental Design of DPX Formulations

Based on preliminary data, the factors of ALA percentage in zein ($X_1$), PVA percentage concentration ($X_2$) and stirring rate ($X_3$) were selected to study their effect on the particle size ($Y_1$), zeta potential ($Y_2$), initial DPX release ($Y_3$) and cumulative DPX release ($Y_4$) of the prepared formulations. The Box-Behnken design was suggested for the development of DPX formulations using Statgraphics Centurion XV version 15.2.05 software (StatPoint Technologies Inc., Warrenton, Va., USA). The goals for the investigated dependent variables of the experimental design were set to minimize $Y_1$ and maximize $Y_2$, $Y_3$, and $Y_4$. The independent variable levels and the dependent variable constraints are shown in Table 1.

TABLE 1

Independent ($X_1$-$X_3$) and dependent ($Y_1$-$Y_4$) variables of DPX-Zein-ALA nanoparticles formulations utilized in Box-Behnken design

| Independent Variables | Unit | Levels | | |
|---|---|---|---|---|
| | | -1 | 0 | 1 |
| Percentage of ALA in Zein ($X_1$) | % | 15 | 20 | 25 |
| Percentage of PVA ($X_2$) | % | 0.5 | 1 | 1.5 |
| Stirring rate ($X_3$) | rpm | 800 | 1000 | 1200 |
| Dependent variables | Unit | Constraints | | |
| | | Low | High | Goal |
| Particle size ($Y_1$) | nm | 148.6 | 206.8 | Minimize |
| Zeta potential ($Y_2$) | mV | 0.294 | 19.1 | Maximize |
| Initial DPX release after 1 h ($Y_3$) | % | 18.09 | 35.67 | Maximize |
| Cumulative DPX release after 24 h ($Y_4$) | % | 79.05 | 97.65 | Maximize |

Abbreviations: DPX; dapoxetine, ALA; alpha lipoic acid, PVA; polyvinyl alcohol.

Preparation of DPX-Loaded NPs

Fifteen different formulations of DPX-loaded NPs were prepared. Briefly, 30 mg of 1E) DPX, and 100 mg of the specified weight of three different "ALA in zein" mixtures (see Definitions) as described in Table 2 (i.e. 15, 20 or 25% ALA in zein) were stirred in 30 mL of methanol at 1000 rpm at room temperature until completely solubilized. The methanolic solution was gradually added to 45 mL of an aqueous solution of PVA (0.5-1.5% w/v) and stirred for 4 hours, then rotated in a rotary evaporator until complete evaporation of the methanol. The colloidal NP dispersion was centrifuged at 20,000 rpm for 45 minutes at 8° C. and washed with deionized water, then lyophilized using freeze dryer Alpha1-2/LD Plus (Martin Christ, Osterode am Harz, Germany) for 72 hours Mannitol (5% w/v) was added to the colloidal dispersion as a cryoprotectant and finally the NPs were stored until fully characterized.

TABLE 2

Formulation variables ($X_1$-$X_3$) of DPX-Zein-ALA nanoparticles and the resulting responses ($Y_1$-$Y_4$).

| | Independent variables | | | Dependent variables | | | |
|---|---|---|---|---|---|---|---|
| Run # | Percentage of ALA in Zein ($X_1$) | Percentage of PVA ($X_2$) | Stirring rate ($X_3$) | Particle size ($Y_1$) | Zeta potential ($Y_2$) | Initial DPX release after 1 h ($Y_3$) | Cumulative DPX release ($Y_4$) |
| DN-1 | 15 | 1.5 | 1000 | 155.6 | 17.3 | 29.68 | 97.32 |
| DN-2 | 15 | 0.5 | 1000 | 159.7 | 19.1 | 31.34 | 97.65 |
| DN-3 | 20 | 0.5 | 800 | 168.9 | 15.2 | 24.34 | 93.76 |
| DN-4 | 25 | 1.0 | 800 | 205.7 | 0.41 | 19.1 | 87.61 |
| DN-5 | 20 | 1.5 | 800 | 163.8 | 10.6 | 26.1 | 96.99 |
| DN-6 | 25 | 0.5 | 1000 | 206.8 | 0.41 | 18.09 | 79.05 |
| DN-7 | 20 | 0.5 | 1200 | 150.1 | 15.1 | 33.45 | 96.95 |
| DN-8 | 15 | 1.0 | 1200 | 148.6 | 17.9 | 35.67 | 97.03 |
| DN-9 | 25 | 1.5 | 1000 | 194.7 | 0.29 | 22.7 | 88.2 |
| DN-10 | 25 | 1.0 | 1200 | 196.9 | 0.39 | 20.1 | 89.4 |
| DN-11 | 20 | 1.5 | 1200 | 160.2 | 13.6 | 30.21 | 96.55 |
| DN-12 | 15 | 1.0 | 800 | 167.3 | 18.0 | 23.54 | 93.21 |
| DN-13 | 20 | 1.0 | 1000 | 179.1 | 14.6 | 28.48 | 89.54 |

TABLE 2-continued

Formulation variables ($X_1$-$X_3$) of DPX-Zein-ALA nanoparticles and the resulting responses ($Y_1$-$Y_4$).

| | Independent variables | | | Dependent variables | | | |
|---|---|---|---|---|---|---|---|
| Run # | Percentage of ALA in Zein ($X_1$) | Percentage of PVA ($X_2$) | Stirring rate ($X_3$) | Particle size ($Y_1$) | Zeta potential ($Y_2$) | Initial DPX release after 1 h ($Y_3$) | Cumulative DPX release ($Y_4$) |
| DN-14 | 20 | 1.0 | 1000 | 177.4 | 14.3 | 29.36 | 91.11 |
| DN-15 | 20 | 1.0 | 1000 | 176.9 | 14.7 | 27.12 | 92.89 |

Note:
*The observed values of $Y_1$, $Y_2$, $Y_3$ and $Y_4$ represent the means of three determinations; standard deviations were <5% of the mean and thus were omitted from the table.
Abbreviations:
DPX; dapoxetine, ALA; alpha lipoic acid, $X_1$; percentage of alpha lipoic acid in Zein, $X_2$; percentage of polyvinyl alcohol, $X_3$; stirring rate, $Y_1$; particle size (nm), $Y_2$; zeta potential (mV), $Y_3$; initial DPX release after 1 h (%), $Y_4$; cumulative DPX release after 24 h (%).

DPX-Loaded NPs Characterization
Particle Size and Zeta Potential Analysis

Samples of the prepared NP formulations were diluted with 20 times their volume and vortexed for 1 min and evaluated for particle size, size distribution and zeta potential using Malvern Zetasizer Nano ZSP analyzer (Malvern Panalytical, Enigma Business Park, Malvern, United Kingdom).

Encapsulation Efficiency Percentage

DPX encapsulation efficiency percent (EE %) was determined by dissolving an accurately weighed amount of the NPs formulation in methanol, followed by sonication and filtering. The encapsulation of DPX in the formulation was measured by high-performance liquid chromatography (HPLC), and the percentage was calculated by the following equation:

$$EE\% = \left(\frac{\text{Amount of drug in the formula}}{\text{Amount of drug initially added}}\right) \times 100$$

In Vitro Release of DPX-Loaded NPs

In vitro release study was investigated utilizing a Franz diffusion cell (automated diffusion system, Microette Plus, Hanson research, Chatsworth, Calif., USA) as previously described.[25] Briefly, the specified weight of DPX-loaded NPs in the donor compartment above the diffusion membrane (0.1 µm, PALL Corporation, NY, USA) was allowed to diffuse into phosphate-buffered saline pH 7.0 in the receptor compartment. Samples were withdrawn at predetermined time intervals for 48 h and analyzed for DPX using an Agilent 1200 HPLC system with a quaternary pump, autosampler and diode-array detector (DAD) (Agilent Technologies, Waldbronn, Germany) The separation process was carried out utilizing an Agilent Zorbax Eclipse Plus C18 column, 3.5 4.6×250 mm (Agilent Technologies, Santa Clara, Calif., USA) and maintained at 40° C. The mobile phase was acetonitrile: phosphate buffer (0.02M $KH_2PO_4$ adjusted to pH 3 with orthophosphoric acid) (45:55, v/v), with a flow rate of 1 mL/min, and peaks were detected at 210 nm. The injection volume was 50 µl. Methanol was used in the preparation of the stock solution of DPX in the concentration of 2000 µg/ml. The range of DPX concentrations was 8-200 µg/ml and used as working standards in the assay.

DPX-Loaded NP Formulations

Results obtained from the prepared 15 formulations, according to the design, were statistically analyzed with ANOVA and multiple response analysis using Statgraphics software. The predicted formulation was prepared and evaluated and compared to the practically prepared formulation for validation of the results. The DPX-loaded NPs formulation was also examined for particle size, zeta potential and morphology scanning electron microscopy (SEM) and transmission electron microscopy (TEM).

Scanning Electron Microscopy (SEM)

The surface of the DPX-loaded NPs was explored after lyophilization using SEM. The sample was mounted on metal stubs with conductive silver paint, sputtered with gold and investigated using SEM (Philips XL30; FBI, Hillsboro, Oreg., USA).

Transmission Electron Microscopy (TEM)

A sample of the DPX-loaded NPs was exposed to a TEM (Model JEM-1230, JOEL, Tokyo, Japan). A drop of the diluted NPs dispersion was added onto a microscope grid, stained with 1% phosphotungstic acid and then dried before investigation.

Pharmacokinetics Evaluation in Healthy Human Volunteers

The pharmacokinetic parameters of the DPX-loaded NPs were evaluated and compared with the marketed DPX tablet as a reference (SPIMACO, Al-Qassim, Saudi Arabia), following oral administration of a single dose (30 mg of DPX) by healthy male volunteers. An open-label, single-dose, randomized, one-period, parallel design was used in which two weeks of screening preceded 24 h study periods as previously described.[23] Briefly, the single-dose investigation was performed in the Egyptian Research and Development Company (ERDC), Cairo, Egypt. The study protocol was approved by the Research Ethical Committee (Protocol code: 0569/452) in agreement with the Declaration of Helsinki and the International Conference on "Harmonisation of Good Clinical Practices". Informed consents were obtained before volunteers were allowed to participate in the study. The prepared DPX-loaded NPs and the commercial DPX tablet were administered orally (30 mg, DPX). Twelve Egyptian male volunteers (25-43 years) participated in this study and were divided into two groups (6 each). Blood samples (5 mL) were collected at 0, 0.16, 0.25, 0.5, 0.75, 1, 1.25, 1.5, 2, 2.5, 3, 4, 6, 8, 12, and 24 h and centrifuged at 3500 rpm for 10 min.

Chromatographic Conditions for DPX Analysis in Human Plasma

An HPLC-MS/MS analytical method was developed at the ERDC laboratories for the determination of DPX in human plasma.[23] Assay linearity was verified for DPX at 2-500 ng/mL with a regression coefficient ($R^2$=0.994). The HPLC-MS/MS system consisted of HPLC Agilent series 1200 (Agilent Technologies Deutschland GmbH, Waldbronn, Germany) system with a mass spectrometer detector (Agilent 6420) Triple Quad G1311A quaternary pump, G1329A autosampler, G1322A vacuum degasser, and mass hunter software. A mixture of 75% acetonitrile: 25% buffer (ammonium formate 20 mM+0.2% (v/v) formic acid in water) was used as a mobile phase at a flow rate of 0.35 ml/min. The reversed-phase column Intersil ODS −3 (4.6 mm×50 cm, dp 5 μm Sigma-Aldrich, USA) was temporized at 25° C. Sildenafil was used as an internal standard (IS).

Pharmacokinetic Data Analysis

Noncompartmental analysis was utilized to calculate the pharmacokinetic (PK) parameters using Kinetica® software (version 4; Thermo Electron Corp., Waltham, Mass., USA). The difference between the two investigated groups in terms of drug plasma concentration was calculated by two-way ANOVA followed by Sidak's multicomparison test using GraphPad Prism 6 Software, Inc. (CA, USA). Unpaired t-test (two-tailed) was used to determine the significance between the pharmacokinetic parameters. The peak plasma concentration of the drug ($C_{max}$), the time required for drug to reach the maximum plasma concentration ($t_{max}$), the area under the time-concentration curve (AUC), elimination rate constant ($K_{el}$) and mean drug residence time (MRT) were calculated from which the relative bioavailability [($AUC_{test}$/$AUC_{reference}$)×100] was determined.

Results and Discussions

The objective of this study was to create DPX-loaded NPs with improved DPX absorption and maximized oral bioavailability. The predefined critical quality features of the DPX-loaded NPs were particle size, zeta potential, and DPX release pattern. Minimizing the particle size of the prepared NPs would allow for increased permeability and absorption via the mucosal membranes. Therefore, we conducted studies to manipulate the factors affecting the NPs formulation to minimize the nanoparticle size, maximize zeta potential, while maximizing drug release. We then verified the efficiency of the DPX-loaded NPs by conducting pharmacokinetic studies in human volunteers after oral administration of a single dose and compared the result with a marketed DPX tablet.

DPX-Loaded NPs Formulation and Characterization

Particle size and zeta potential are key parameters for evaluation of NPs stability and efficiency which influence the biopharmaceutical feature of NPs.

Particle Size ($Y_1$)

As reported previously in several studies, the physicochemical properties of NPs (nano-size range of the particles) rather than the drug itself, determines the release profile and absorption of the drug.[26-28] Due to their nano-size range, NPs have large surface areas available for absorption via the epithelial surfaces.[29,30]

Table 2 shows the variabilities in the size of the prepared NP formulations which ranged from to 206.8 nm for DN-8 and DN-6, and with respect to changes of the investigated factors, the results are displayed in Table 3. Two-way ANOVA analyses showed a significant synergistic effect of the percentage of ALA in Zein ($X_1$) on the particle size ($Y_1$) with a p-value of 0.0001. While the stirring rate ($X_3$) was found to have a significant antagonistic effect on $Y_1$ with a p-value of 0.0041. Also, it was noticed that the quadratic term of $X_1$ had a significant synergistic effect on $Y_1$ with a p-value of 0.0027. Finally, it was noticed that $Y_1$ was significantly affected by the quadratic term of $X_2$ and $X_3$ with p values of 0.0050 and 0.0062, respectively. The prediction model to correlate variables with the obtained sizes is shown below:

$$Y_1 = 116.275 - 13.5725X_1 + 45.1X_2 + 0.29694X_3 + 0.4055X_1^2 - 0.8X_1X_2 + 0.0025X_1X_3 - 34.95X_2^2 + 0.038X_2X_3 - 0.0002X_3^2 \quad \text{equation (2)}$$

TABLE 3

Statistical analysis of variance (ANOVA) of the responses ($Y_1$-$Y_4$) results

| Factors | Particle size ($Y_1$) | | Zeta potential ($Y_2$) | | Initial DPX release after 1 h ($Y_3$) | | Cumulative DPX release after 24 h ($Y_4$) | |
|---|---|---|---|---|---|---|---|---|
| | Estimate | P-Value | Estimate | P-Value | Estimate | P-Value | Estimate | P-Value |
| $X_1$ | 43.225 | 0.0001* | −17.703 | 0.0001* | −10.06 | 0.0001* | −10.238 | 0.0032* |
| $X_2$ | −2.8 | 0.3123 | −2.002 | 0.0189* | 0.368 | 0.6257 | 2.913 | 0.1923 |
| $X_3$ | −12.475 | 0.0041* | 0.693 | 0.2903 | 6.588 | 0.0002* | 2.09 | 0.3290 |
| $X_1^2$ | 20.275 | 0.0027* | −9.704 | 0.0001* | −6.79 | 0.0013* | −4.875 | 0.1473 |
| $X_1X_2$ | −4.0 | 0.3079 | 0.842 | 0.3565 | 3.135 | 0.0259* | 4.74 | 0.1435 |
| $X_1X_3$ | 4.95 | 0.2192 | 0.041 | 0.9625 | −5.565 | 0.0026* | −1.015 | 0.7257 |
| $X_2^2$ | −17.475 | 0.0050* | −0.810 | 0.3907 | 1.055 | 0.3576 | 3.625 | 0.2587 |
| $X_2X_3$ | 7.6 | 0.0836 | 1.545 | 0.1214 | −2.5 | 0.0546 | −1.815 | 0.5361 |
| $X_3^2$ | −16.625 | 0.0062* | −1.001 | 0.2984 | −0.645 | 0.5629 | 6.14 | 0.0834 |
| $R_2$ | 98.8063 | | 99.529 | | 98.7042 | | 89.9672 | |
| Adj. $R^2$ | 96.6577 | | 98.6813 | | 96.3719 | | 71.9082 | |
| SEE | 3.52484 | | 0.828797 | | 1.00074 | | 2.7339 | |
| MAE | 1.75667 | | 0.409478 | | 0.462667 | | 1.39367 | |

Note:
*Significant effect of factors on individual responses.
Abbreviations:
DPX; dapoxetine, ALA; alpha lipoic acid, $X_1$; percentage of alpha lipoic acid in Zein, $X_2$; percentage of polyvinyl alcohol, $X_3$; stirring rate, $Y_1$; particle size (nm), $Y_2$; zeta potential (mV), $Y_3$; initial DPX release after 1 h (%), $Y_4$; cumulative DPX release after 24 h (%); $X_1X_2$, $X_1X_3$, $X_2X_3$, the interaction term between the factors; $X_1X_1$, $X_2X_2$, and $X_3X_3$ are the quadratic terms between the factors; $R^2$, R-squared; Adj-$R^2$, Adjusted R-squared; SEE, standard error of estimate; and MAE, Mean absolute error.

Figure 1A:
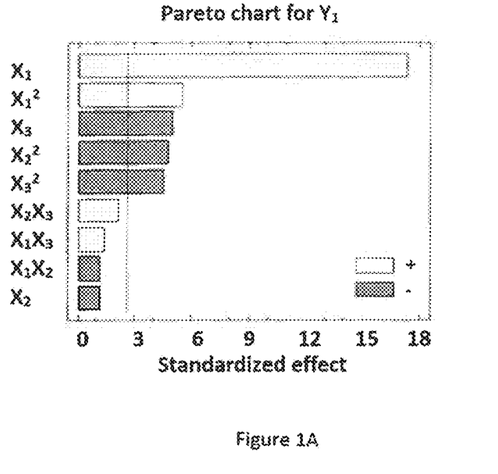
FIG. 1A-D. Standardized Pareto charts showing the significance of X1, X2 and X3 and their combined effects on Y1 (A); Y2 (B); Y3 (C) and Y4 (D). Abbreviations: X1; percentage of alpha lipoic acid in zein, X2; polyvinyl alcohol % concentration, X3; stirring rate, Y1; particle size (nm), Y2; zeta potential (mV), Y3; initial permeation after 1 h (%), Y4; cumulative permeation after 24 h (%).
Figure 2A:
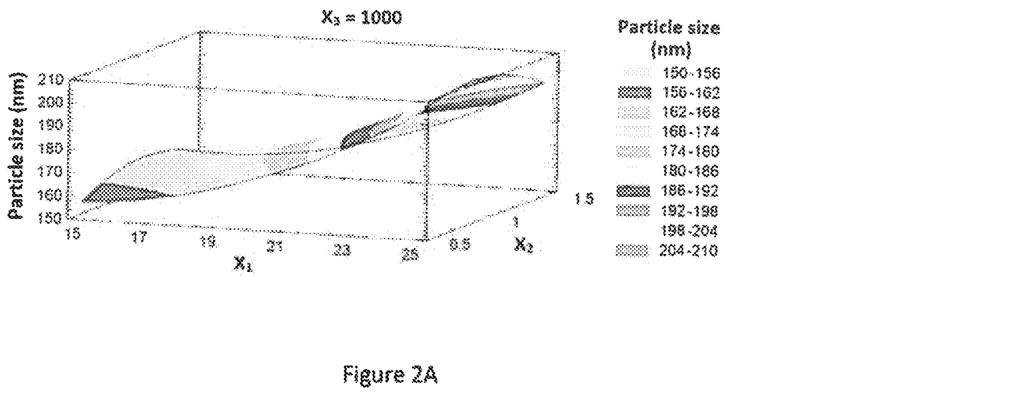
FIG. 2A-F. 3D response surface plots showing the effects of X1, X2 and X3 on the investigated dependent variables Y1 (A & B); Y2 (C); Y3 (D&E) and Y4 (F). X1; percentage of alpha lipoic acid in Zein, X2; polyvinyl alcohol % concentration, X3; stirring rate, Y1; particle size (nm), Y2; zeta potential (mV), Y3; initial release after 1 h (%), Y4; cumulative release after 24 h (%).
Figure 2B:
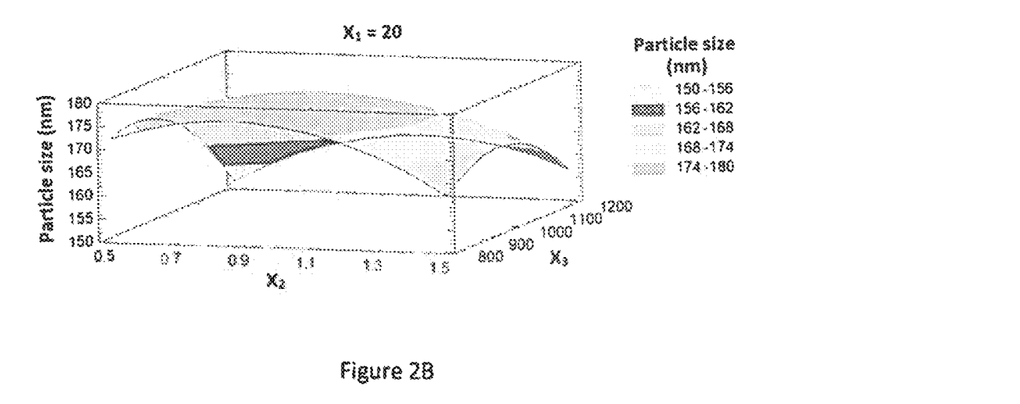

We observed that increasing ALA percentage in the polymer content of the formulations led to a significant increase in the particle size of the NPs as observed in the formulations DN-4, DN-6, DN-9, and DN-10. This may be explained by the formation of aggregates due to interactions between ALA and Zein matrix.[31] Conversely, increasing the percentage of Zein in the polymeric matrix resulted in the formation of smaller size NPs, likely due to the presence of charged amino acids in the Zein structure.[32,33] At pH 7.2, the protein molecules aggregated into small size particles with reduced void spaces, enhancing NPs formation and hindering large aggregation via acceleration of thiol-disulfide interchange reaction.[15] Another possible explanation may be related to the structural configuration of hydrophilic and hydrophobic regions on Zein surface. Zein molecules associated into an elongated prism-like shape with hydrophobic sides and hydrophilic tops and bottoms,[34] allowing Zein molecules to associate in a side-by-side manner to form many small NPs. This direct relationship between $X_1$ and the particle size ($Y_1$) are presented in the Pareto chart and response surface plots of $Y_1$ (FIGS. 1A and 2A&B).

We observed an inverse relationship between the stirring rate ($X_3$) and the average particle size ($Y_1$). The particle size increased from 150.1 to 168.9 nm in DN-7 and DN-3, respectively when the stirring rate was decreased from 1200 to 800 rpm at an equal level of $X_1$ and $X_2$. Also, the particle size increased from 196.9 to 205.7 nm in DN-10 and DN-4, respectively by decreasing $X_3$ from 1200 to 800 rpm at the same level of $X_1$ and $X_2$. We also observed an increase of $Y_1$ from 148.6 to 167.3 nm for DN-8 and DN-12, respectively with a decrease in $X_3$ from 1200 to 800 rpm at the same level of $X_1$ and $X_2$. This finding could be explained by increasing the shearing action and reducing the tendency of a collision between the formed NPs and decreasing the possibility for aggregation that leads to smaller particle size.[35-37]

Zeta Potential ($Y_2$)

Figure 1B:
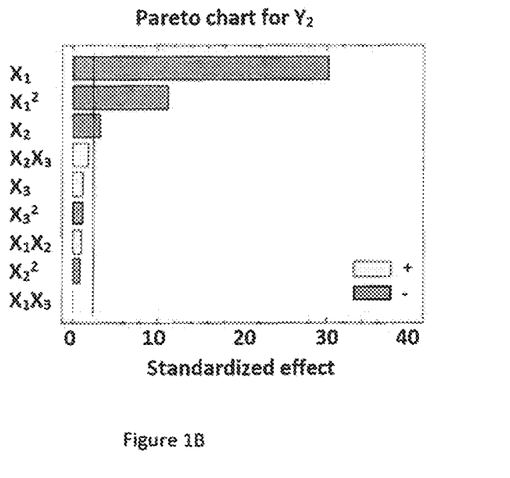
Figure 2C:
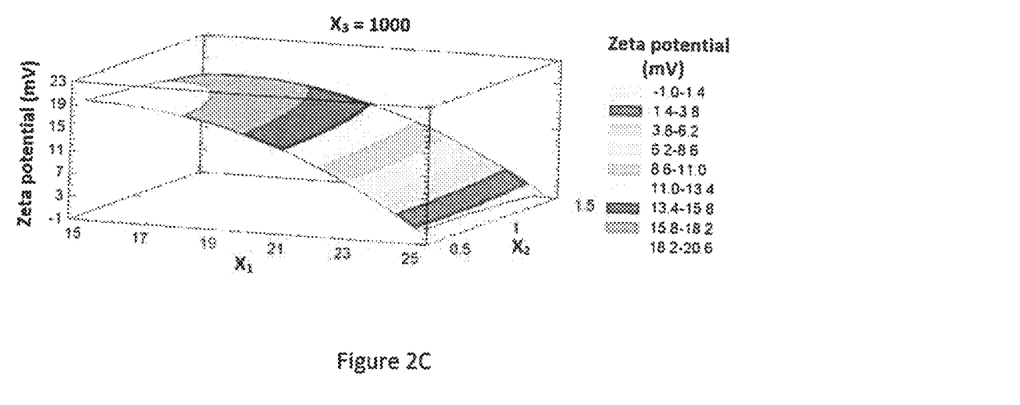
Figure 2D:
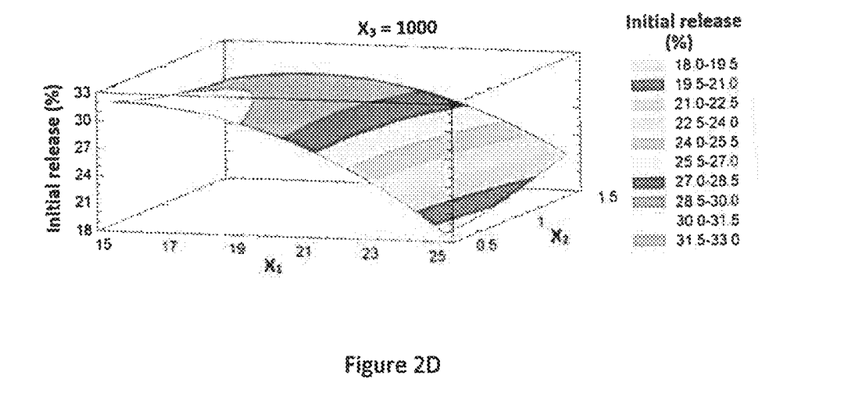
Figure 2E:
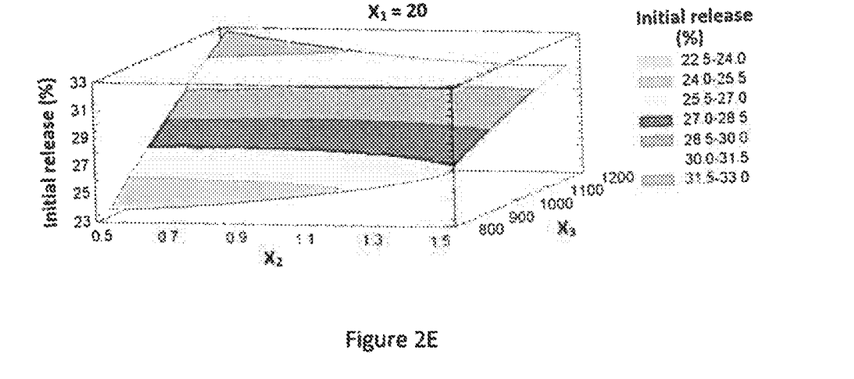
Figure 2F:
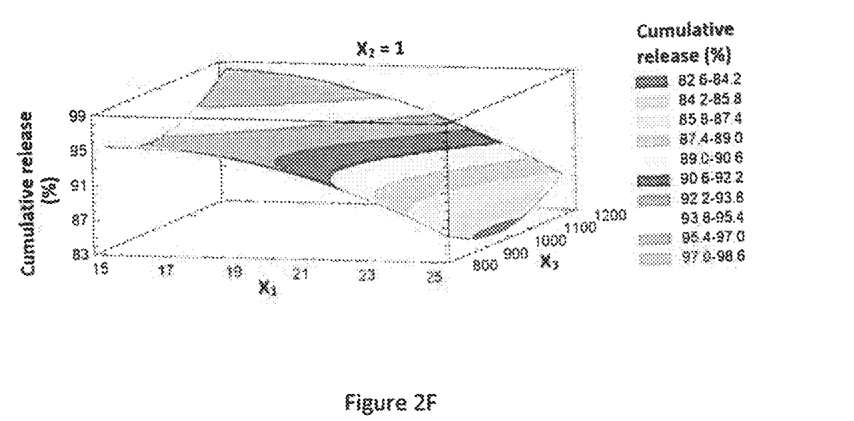

Zeta potential represents a key indicator for the stability of the colloidal dispersions. The values of zeta potential of all NP formulations (Y2) was in the range from 0.29 mV for DN-9 to 19.1 mV for DN-2 (Table 2). In general, all formulations were considerably stable except the formulations containing a high percentage of ALA (25%). It was clear that $X_1$ (percentage of ALA in Zein) and $X_2$ (percentage of PVA) were the main factors responsible for the difference in the zeta potential of DPX-loaded NPs as shown in FIGS. 1B and 2C. Multiple regression analysis indicated that both $X_1$ and $X_2$ had significant inverse effects on the zeta potential ($Y_2$) with a more predominant effect on $X_1$ with p values of 0.0001 and 0.0189, respectively (Table 3). The prediction equation of zeta potential value is:

$$Y_2 = -30.0548 + 5.804X_1 - 9.8487X_2 + 0.0186X_3 - 0.19408X_1^2 + 0.1683X_1X_2 + 0.00002X_1X_3 - 1.6207X_2^2 + 0.0077X_2X_3 - 0.00001X_3^2 \quad \text{equation (3)}$$

It was evident that an increased percentage of ALA in the polymeric matrix led to a marked decreased in the zeta potential of the prepared NPs. The zeta potential value of formulations containing 15% of ALA is close to 20 mV while in the formulations containing 25% of ALA it is less than 1. An increase in $X_1$ from 15 to 25%, at the same level of $X_2$ and $X_3$, led to a decrease in zeta potential from 17.3 to 0.29 mV for DN-1 and DN-9, respectively. The same finding was observed in DN-2 and DN-6 by decreasing the zeta potential from 19.1 to 0.41 mV, respectively. Also, this finding could be confirmed by the decrease of Y2 from 18.0 to 0.41 mV for DN-12 and DN-4, respectively. We attribute these observations to increased adsorption of ALA on the surface of NPs (observed with zeta potential measurement) that could neutralize the positive charges of Zein NPs. The positive charge on Zein NPs was found to decrease when the percentage of ALA increased in the polymeric matrix. The adsorption of ALA with its anionic free fatty acids on the formed cationic Zein surfaces could neutralize their positive charge.[38]

Despite a lesser effect of $X_2$ than $X_1$ on $Y_2$, it was found that increasing $X_2$ from 0.5 to 1.5%, at the same level of $X_1$ and $X_2$, led to the decrease in zeta potential from 19.1 to 17.3 mV for DN-2 and DN-1, respectively. The same finding was observed in DN-7 and DN-11 by decreasing the zeta potential from 15.1 to 13.6 mV, respectively. Also, this finding was confirmed by the decrease of Y2 from 15.2 to 10.6 mV for DN-3 and DN-5, respectively. This observation could be attributed to incomplete hydrolysis of the starting material resulting in a number of acetic groups that are capable of ionizing and reducing the positive charge that affects zeta potential of the prepared nanoparticles.[40]

DPX Encapsulation Efficiency %

The data for DPX EE % showed no significant change in EE % among the prepared formulations with an average value of 34.35±4.66%. DPX is mainly charged at physiological pH with its pKa of 8.6. The protonation of DPX is attributed to the elevated aqueous solubility (68 mg/mL) that contributes to the reduction of EE %.

In Vitro Release Behavior of DPX from NP Formulations ($Y_3$ and $Y_4$)

Figure 1C:
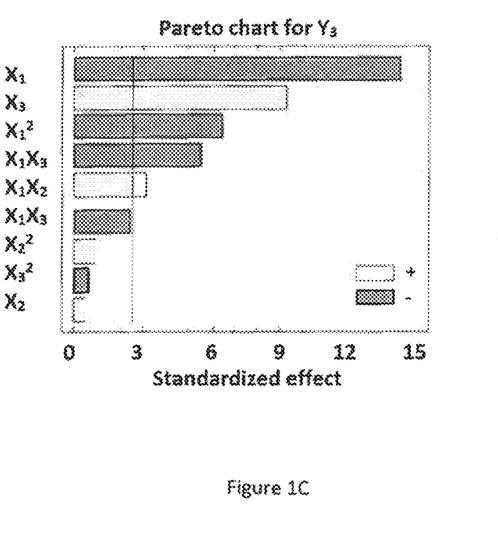
Figure 1D:
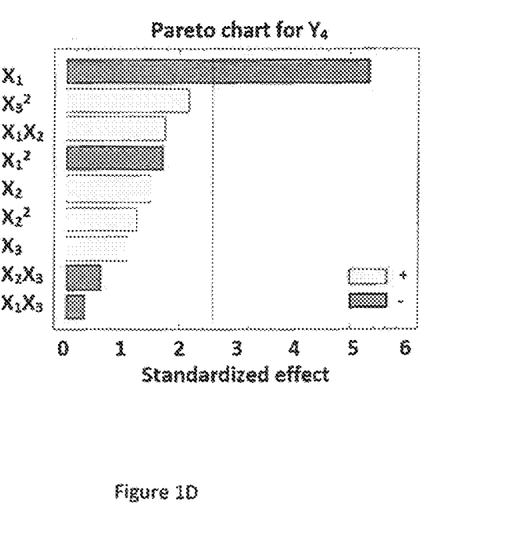
Figure 3A:
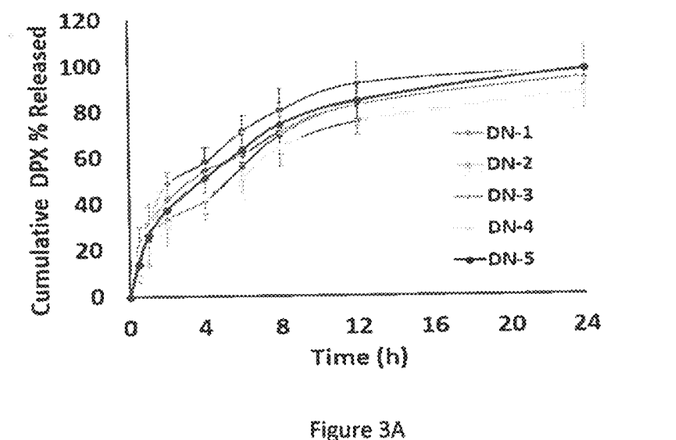
FIG. 3A-C. In vitro release profiles of DPX-loaded NPs formulations: (A) F1-F5; (B) F6-F10; and (C) F11-F15.
Figure 3B:
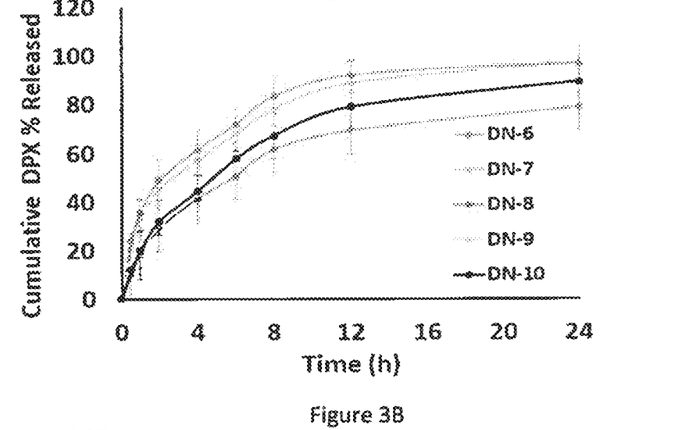
Figure 3C:
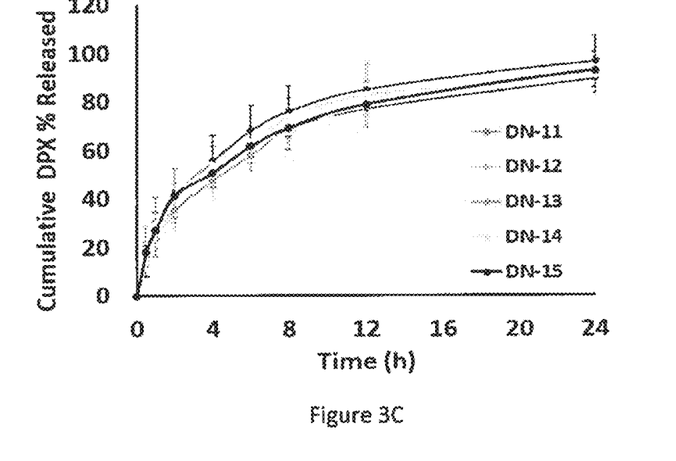

This study was conducted to predict the in vivo behavior of the nanoparticle. The in vitro release of DPX from the prepared NPs formulations (DN-1 to DN-15) showed a biphasic form with an initial rapid release followed by a controlled release phase (FIG. 3). The initial release after 1 hour ranged from 18.09% with DN-6 to 35.67% with DN-8 (Table 2), whereas, the cumulative % of DPX released after 24 hours showed DN-2 to have the most release (97.65) with DN-6 showing the least release (79.05%) (Table 2). Regression analysis with ANOVA detected that both $Y_3$ and $Y_4$ are governed by the percentage of ALA in Zein ($X_1$), which had a significant antagonistic effect on $Y_3$, and $Y_4$ with p values of 0.0001, and 0.0032, respectively (Table 3 and FIGS. 1C&D and 2D, E&F). Also, the stirring rate ($X_3$) was found to have a significant antagonistic effect on the initial DPX release percentage after 1 h ($Y_3$) with a p-value of 0.0002. In addition, the quadratic term of $X_1$ had a significant antagonistic effect on Y3 with a p-value of 0.0013. Finally, the initial DPX release percentage after 1 h ($Y_3$) was significantly affected by the interaction terms $X_1X_2$ and $X_1X_3$ with p values of 0.0259 and 0.0026, respectively. The equations (equations 4&5) predicted the responses $Y_3$ and $Y_4$:

$$Y_3 = -84.2788 + 6.5815X_1 - 3.8925X_2 + 0.1007X_3 - 0.1358n + 0.627X_1X_20.00278X_1X_3 + 2.11X_2^2 - 0.0125X_2X_3 - 0.000008X_3^2 \quad \text{equation (4)}$$

$$Y_4 = 148.252 + 2.4358X_1 - 21.4725X_2 - 0.12905X_3 - 0.0975X_1^2 + 0.948X_1X_2 - 0.0005X_1X_3 + 7.25X_2^2 - 0.009X_2X_3 + 0.00008X_3^2 \quad \text{equation (5)}$$

Data obtained from the release profiles (Table 2 and FIG. 3) indicate that increases in the percentage of ALA in the polymeric matrix ($X_1$) significantly impacted both the initial and cumulative DPX release. An increase in $X_1$ from 15 to 25%, at the same level of $X_2$ and $X_3$, led to a decrease in $Y_3$ from 29.68 to 22.7% for DN-1 and DN-9, respectively. A similar observation was found for DN-2 and DN-6 where Y3 decreased from 31.34 to 18.09%, and 23.54 to 19.1% for DN-12 and DN-4, respectively. The same formulations revealed a similar trend regarding the cumulative DPX release ($Y_4$). Without being bound by theory, it is believed that this behavior may explained by the release of surface bound DPX from Zein-loaded NPs during the initial rapid release phase, and DPX diffusion from the NP core may be responsible for the controlled release phase. In addition, the hydrophobic nature of Zein and ALA NPs can contribute to the sustained release of encapsulated DPX.

Moreover, it was found that there is a direct relationship between the stirring rate ($X_3$) and the initial DPX release ($Y_3$). The initial DPX release decreased from 20.1 to 19.1% in DN-10 and DN-4, respectively when the stirring rate was decreased from 1200 to 800 rpm at an equal level of $X_1$ and $X_2$. Also, $Y_3$ decreased from 35.67 to 23.54% in DN-8 and DN-12, respectively by decreasing $X_3$ from 1200 to 800 rpm at the same level of $X_1$ and $X_2$. We observed a similar decrease of Y3 from 33.45 to 24.34% for DN-7 and DN-3, respectively due to the decrease in $X_3$ from 1200 to 800 rpm at the same level of $X_1$ and $X_2$. This finding may be due to the size reduction of the NPs by increasing the stirring rate, which permits greater contact between the particle surface area and the dissolution media, promoting penetration of NPs and consequently improving the drug dissolution and increasing the initial drug release.

Validation of DPX-Loaded NPs

Figure 4A:
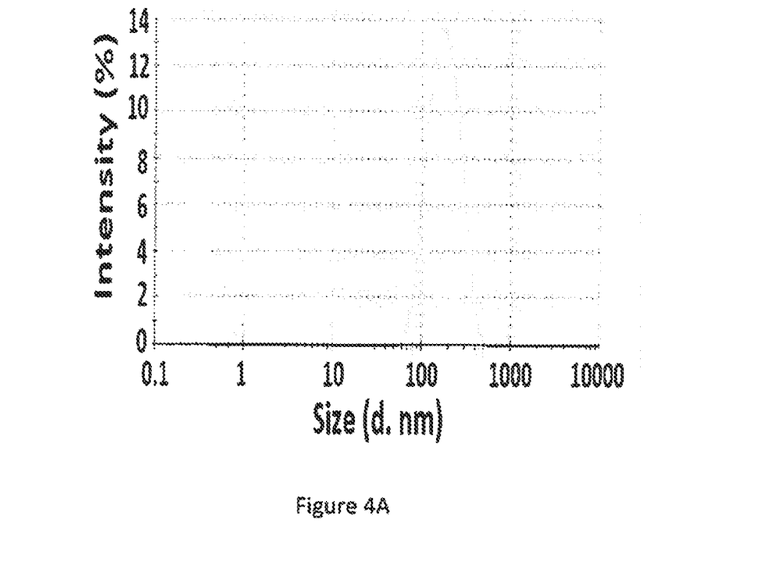
FIG. 4A-F. Particle size distribution (A), zeta potential (B) measured by particle size analyzer, SEM photomicrographs (C&D) and TEM images (E&F) of DPX-loaded NPs. Abbreviations: TEM; Transmission electron microscope.
Figure 4B:
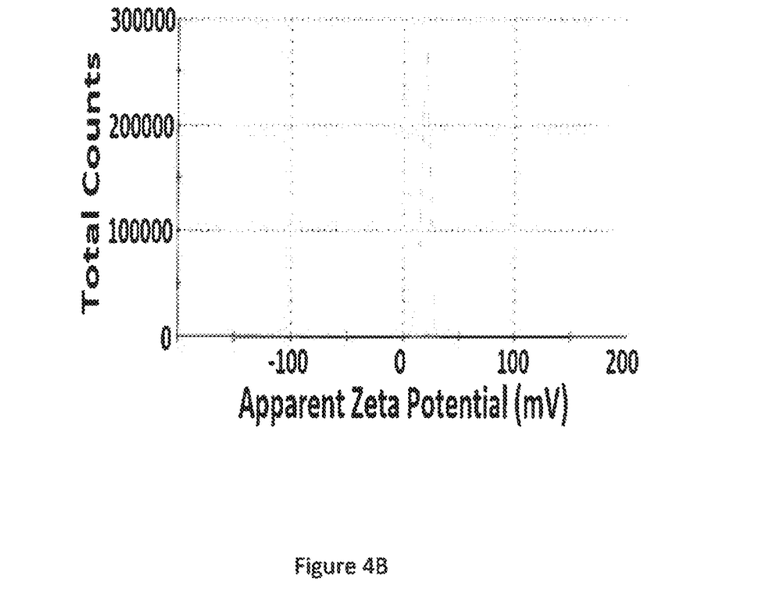

The results indicated that a combination of independent factors for the DPX-loaded NPs formulation showed the desired particle size of 159.24 nm with polydispersity index value of 0.140 (FIG. 4A) and zeta potential of 19.14 mV (FIG. 4B). In addition, the formulation releases 25.32% of its DPX content in the first hour and 95.89% after 24 hours. The results of the observed and the predicted values are shown in Table 4. The predicted error percentage of the responses were less than 6%.[41]

TABLE 4

Calculated variables and observed, predicted and residual values for responses ($Y_1$-$Y_4$).

| Factor | Value | Response | Predicted | Observed | Residual |
|---|---|---|---|---|---|
| $X_1$ (%) | 15 | $Y_1$ (nm) | 161.88 | 159.24 | 2.64 |
| $X_2$ (%) | 0.5 | $Y_2$ (mV) | 19.49 | 19.14 | 0.35 |
| $X_3$ (rpm) | 800 | $Y_3$ (%) | 24.22 | 25.32 | 1.10 |
| | | $Y_4$ (%) | 97.19 | 95.89 | 1.29 |

Abbreviations: $X_1$; percentage of alpha lipoic acid in zein, $X_2$; polyvinyl alcohol % concentration, $X_3$; stirring rate, $Y_1$; particle size (nm), $Y_2$; zeta potential (mV), $Y_3$; initial permeation after 1 h (%), $Y_4$; cumulative permeation after 24 h (%).

Morphological Examination of the DPX-Loaded NPs

Figure 4C:
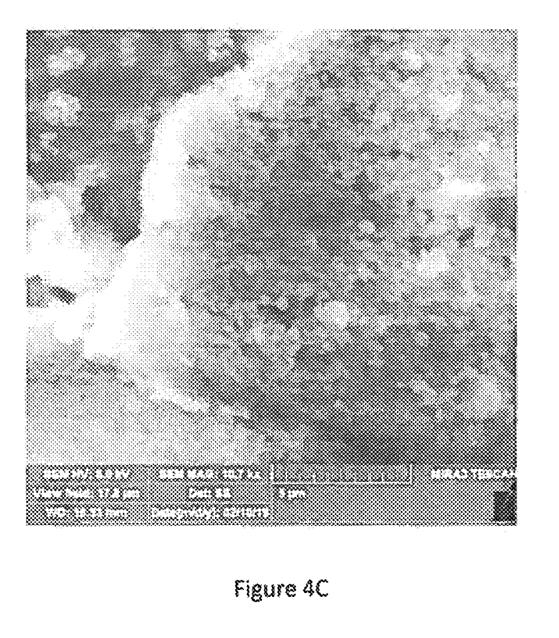
Figure 4D:
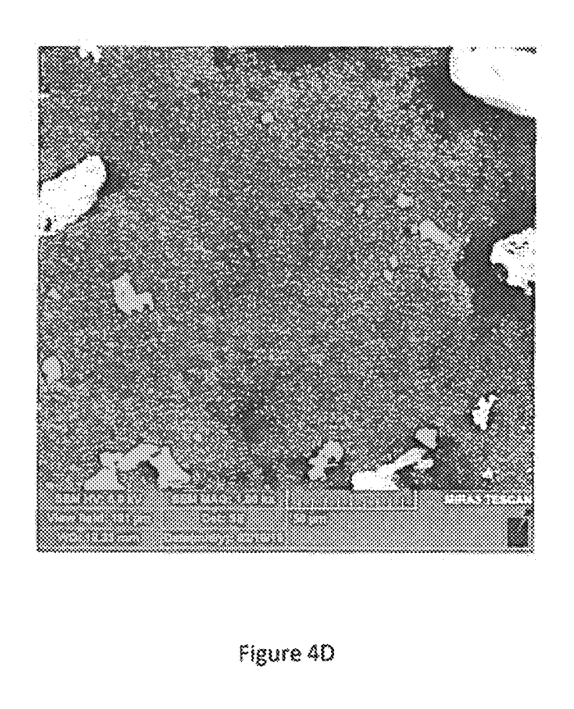
Figure 4E:
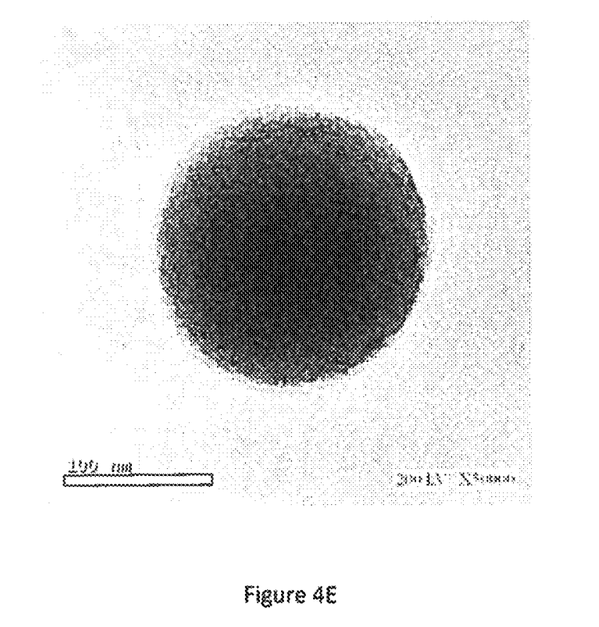
Figure 4F:
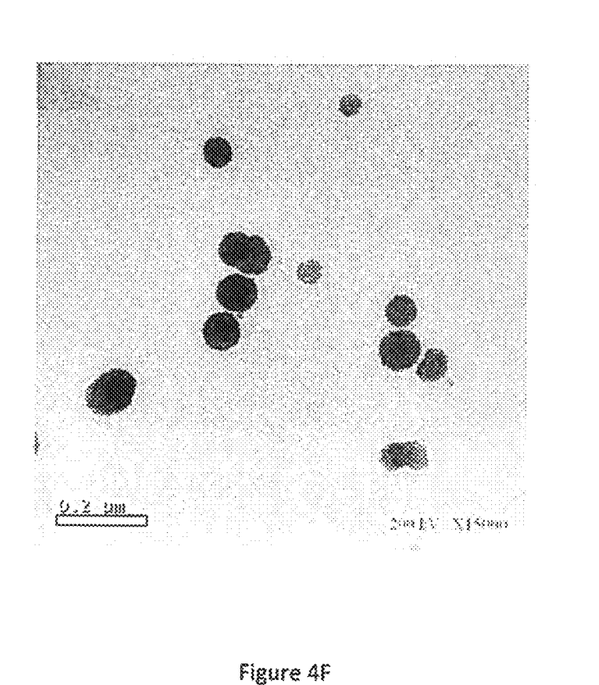

We undertook a morphological examination of the DPX-loaded NPs to confirm their spherical morphology. SEM photomicrographs at different magnifications (FIGS. 4C&D) revealed the spherical shape and the smooth surface of the DPX-loaded NPs. TEM images (FIGS. 4E&F) confirmed the spherical structure and the dark core of the NPs. No aggregation was observed, and the size of the NPs was in good agreement with that obtained employing dynamic light scattering. The results suggest uniformity of size distribution of the prepared NPs.

Figure 5:
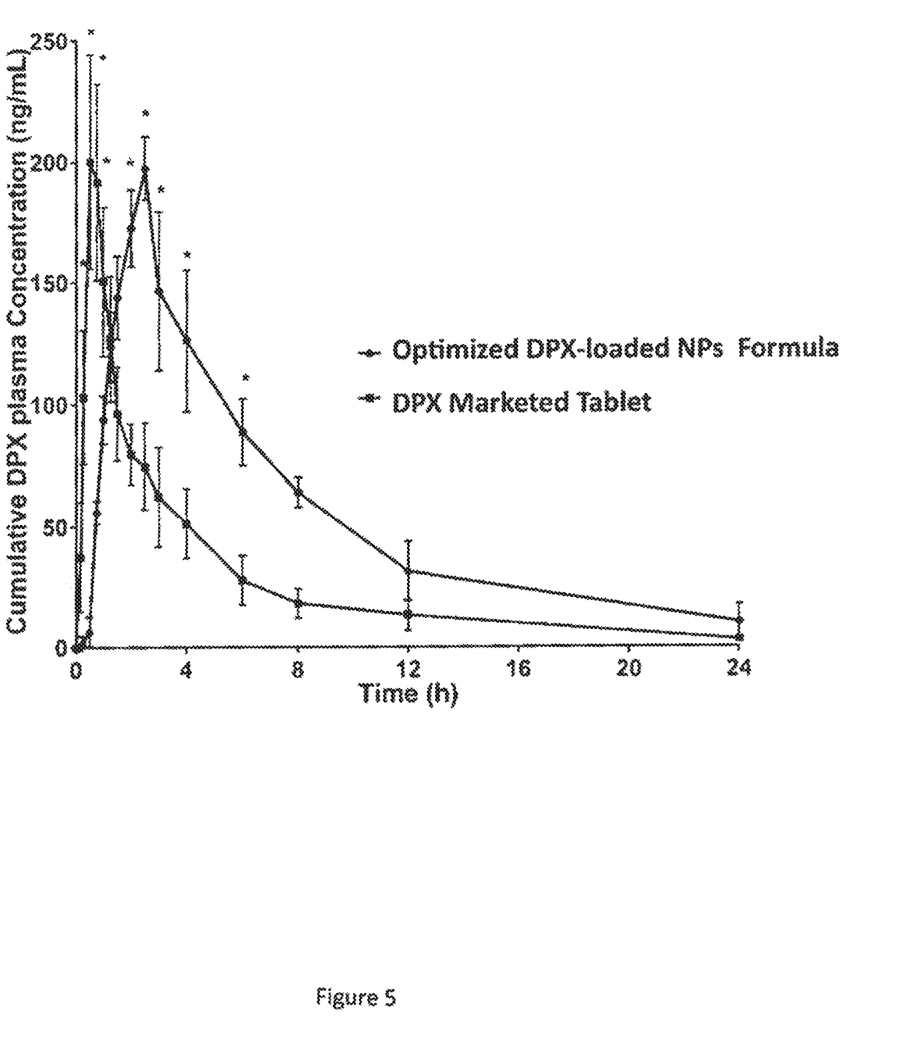
FIG. 5. Plasma concentration—time profiles for the DPX-zein-ALA nanospheres and marketed DPX tablets (30 mg) administered orally as a single dose. Data represent the mean value±standard deviation (n=6). * Significant at P<0.05 (two-way ANOVA, Sidak's multi-comparison test).

Single-Dose Clinical Pharmacokinetics Investigation of the DPX NPs Formulation on Healthy Human Volunteers To study the bioavailability of DPX-loaded NPs, human volunteers were given a single orally administered dose of DPX-loaded NPs equivalent to 30 mg of DPX. The results presented in FIG. 5 and Table 5 show a significant difference (p<0.05) of $t_{max}$, AUC (0-24) and $AUC_{(0-\infty)}$ for DPX-loaded NPs when compared with the marketed DPX tablet. DPX-loaded NPs significantly prolonged $t_{max}$ by 4-fold (2.5±0.314 h vs. 0.583±0.144 h, respectively), AUC by 2-fold, with a slight reduction of $t_{1/2}$ (5.283±1.077 h vs 8.452±2.813 h). On the other hand, the data showed no significant difference (p<0.05) in the $C_{max}$ values of the NP formulation compared with the marketed DPX tablet. Most importantly, the DPX-loaded NPs formulation showed 194% improved relative bioavailability when compared to the marketed tablet. The reduction of DPX half-life ($t_{1/2}$) in the DPX-loaded NPs is most likely due to the improved permeability, absorption and distribution of DPX from the NP formulation to the second compartment tissue. This could be related to reduced particle size (to the nanoscale range) formulation that leads to enhanced DPX oral absorption with rapid elimination. Without being bound by theory, it is believed that the enhancement in the bioavailability is likely due to the prolongation in the MRT of the NPs to 7.637±1.373 h compared to 6.031±1.826 h for the marketed tablet. Prolongation in MRT was accompanied by prolongation in the $t_{max}$ from 0.583±0.144 h of the tablet to 2.5±0.314 h of the NPs. Prolongation of the $t_{max}$ and MRT of the DPX in the NPs could be due to the controlled release behavior of the encapsulated DPX in the NPs. Also, the presence of Zein and ALA in the formulation sterically hinder the uptake of NPs by the tissue through the reticuloendothelial system, decreasing its rate of clearance from the body.[28,43] In addition, the N-terminal region of Zein protein interacts with cell membranes and serves as a peptide carrier for drugs and thus enhances paracellular permeability.[44] These features likely underpin the enhanced bioavailability of the developed DPX-loaded NPs formulation.

TABLE 5

Single dose clinical pharmacokinetic parameters after oral administration of 30 mg of DPX-loaded NPs and DPX marketed tablets

| Pharmacokinetic Parameter | DPX-loaded NPs | DPX Marketed Tablets |
|---|---|---|
| $C_{max}$ (ng/mL) | 197.384 ± 13.153 | 200.121 ± 44.351 |
| $t_{max}$ (h) | 2.5 ± 0.314* | 0.583 ± 0.144 |
| $AUC_{(0-24)}$ (ng · h/mL) | 1290.375 ± 262.169* | 662.758 ± 116.011 |
| $AUC_{(24-\infty)}$ (ng · h/mL) | 85.77 ± 79.191 | 46.419 ± 31.879 |
| $AUC_{(0-\infty)}$ (ng · h/mL) | 1376.145 ± 339.592* | 709.178 ± 146.307 |
| $AUMC_{(0-24)}$ ng · hr²/mL | 8749.718 ± 2815.176 | 3324.778 ± 1226.219 |
| $AUMC_{(24-end)}$ ng · hr²/mL | 2058.471 ± 1900.592 | 1114.068 ± 765.084 |
| $AUMC_{(0-\infty)}$ ng · hr²/mL | 10808.189 ± 4708.753 | 4438.846 ± 1991.228 |
| $K_{el}$ (h⁻¹) | 0.135 ± 0.025 | 0.089 ± 0.032 |
| $t_{1/2}$ (h) | 5.283 ± 1.077 | 8.452 ± 2.813 |
| MRT (h) | 7.637 ± 1.373 | 6.031 ± 1.826 |
| Relative bioavailability (%) | 194.04 | — |

Data represent the mean value ± standard deviation (SD) (n = 6)
*significant at P <0.05 unpaired t test (two-tailed).

CONCLUSIONS

The introduction of DPX for the treatment of PE eliminates the reliance on other non-approved treatments, however, it is fraught with low bioavailability leading to high therapeutic doses and adverse side effects. We have successfully developed a DPX-Zein-ALA formulation that exhibits improved oral bioavailability of DPX in human volunteers when compared to the marketed DPX tablet. These results showed that NP formulations which improve the bioavailability of DPX can be used successfully to treat or prevent male PE.

1. Althof S E, Abdo CHN, Dean J, et al. *International Society for Sexual Medicine's Guidelines for the Diagnosis and Treatment of Premature Ejaculation.* Vol 7. Elsevier Masson SAS; 2010. doi:10.1111/j.1743-6109.2010.01975.x
2. Laumann E O, Nicolosi A, Glasser D B, et al. *Int J Impot Res.* 2004; 17:39. https://doi.org/10.1038/sj.ijir.3901250.
3. Nicolosi A, Laumann E O, Glasser D B, Moreira Jr E D, Paik A, Gingell C. *Urology.* 2004; 64(5):991-997. doi: 10.1016/j.urology.2004.06.055

4. Patel K, Hellstrom WJG. *Curr Opin Investig Drugs.* 2009; 10(7):681-690.
5. Kendirci M, Salem E, Hellstrom W J. *Ther Clin Risk Manag.* 2007; 3(2):277-289.
6. McCarty E, Dinsmore W. *Core Evid.* 2012; 7:1-14. doi:10.2147/CE.S13841
7. McMahon C G. *Ther Adv Urol.* 2012; 4(5):233-251. doi:10.1177/1756287212453866
8. European Medicines Agency. Priligy.
9. Modi N B, Dresser M J, Simon M, Lin D, Desai D, Gupta S. *J Clin Pharmacol.* 2006; 46(3):301-309. doi:10.1177/0091270005284850
10. Thyssen A, Sharma O, Tianmei S, et al. *J Clin Pharmacol.* 2010; 50(12):1450-1460. doi:10.1177/0091270009359183
11. McMahon C G. *Expert Opin Pharmacother.* 2010; 11(10):1741-1752. doi:10.1517/14656566.2010.493174
12. Algandaby M M, Al-Sawahli M M, Ahmed OAA, et al. *J Biomed Nanotechnol.* 2016; 12(9). doi:10.1166/jbn.2016.2270
13. Hashem F M, Al-Sawahli M M, Nasr M, Ahmed OAA. *Int J Nanomedicine.* 2015; 10. doi:10.2147/IJN.S83906
14. Padua G W, Wang Q. In: *ACS Symposium Series.* Vol 1007; 2009:143-156. doi:10.1021/bk-2009-1007.ch009
15. Ahmed OAA, Zidan A S, Khayat M. *Int J Nanomedicine.* 2016; 11:543-555. doi:10.2147/IJN.S99731
16. Corradini E, Curti P S, Meniqueti A B, Martins A F, Rubira A F, Muniz E C. *Int J Mol Sci.* 2014; 15(12): 22438-22470. doi:10.3390/ijms151222438
17. Bouman J, Belton P, Venema P, Van Der Linden E, De Vries R, Qi S. *Pharm Res.* 2016; 33(3):673-685. doi: 10.1007/s11095-015-1818-8
18. Alan C, Kocoglu H, Resit Ersay A, Anil Kurt H, Ertung Y, Alan H. *Actas Urologicas Españolas (English Ed.* 2010; 34(10):874-881. doi:10.1016/S2173-5786(10) 70217-1
19. Caruso S, Iraci Sareri M, Casella E, Ventura B, Fava V, Cianci A. *Minerva Ginecol.* 2015; 67(5):413-419.
20. Hamano Y. *Br Poult Sci.* 2014; 55(3):343-350. doi: 10.1080/00071668.2014.903559
21. Keegan A, Cotter M A, Cameron N E. *Diabetologia.* 1999; 42(3):343-350. doi:10.1007/s001250051161
22. Mitkov M D, Aleksandrova I Y, Orbetzova M M. *Folia Med (Plovdiv).* 2013; 55(1):55-63.
23. Ahmed OAA. *Sci Rep.* 2018; 8(1):15802. doi:10.1038/s41598-018-34235-8
24. Ahmed OAA, El-Say K M, Aljaeid B M, Badr-Eldin S M, Ahmed T A. *Int J Nanomedicine.* 2018; Volume 14:33-43. doi:10.2147/IJN.S187470
25. Ahmed OAA, Afouna M I, El-Say K M, Abdel-Naim A B, Khedr A, Banjar Z M. *Expert Opin Drug Deliv.* 2014; 11(7). doi:10.1517/17425247.2014.906402
26. Doijad R, Manvi F, Godhwani D, Joseph R, Deshmukh N. *Indian J Pharm Sci.* 2008; 70(2):203. doi:10.4103/0250-474X.41456
27. Kim S-H, Lee S H, Lee H J. *Am J Anal Chem.* 2010; 01(03):135-143. doi:10.4236/ajac.2010.13017
28. Aljaeid B M, El-Say K M, Hosny K M. *Drug Dev Ind Pharm.* 2019; 45(7):1130-1139. doi:10.1080/03639045.2019.1597105
29. He C, Yin L, Tang C, Yin C. *Biomaterials.* 2012; 33(33):8569-8578. doi:10.1016/j.biomaterials.2012.07.063
30. El-Say K M, El-Sawy H S. *Int J Pharm.* 2017; 528(1-2):675-691. doi:10.1016/j.ijpharm.2017.06.052
31. Weerakody R, Fagan P, Kosaraju S L *Int J Pharm.* 2008; 357(1-2):213-218. doi: 10.1016/j.ijpharm.2008.02.019
32. Bugs M R, Forato L A, Bortoleto-Bugs R K, et al. *Eur Biophys J.* 2004; 33(4):335-343. doi:10.1007/s00249-003-0354-3
33. Muthuselvi L, Dhathathreyan A. *Colloids Surfaces B Biointerfaces.* 2006; 51(1):39-43. doi:10.1016/j.colsurfb.2006.05.012
34. Matsushima N, Danno G I, Takezawa H, Izumi Y Biochim Biophys Acta—Protein Struct Mol Enzymol. 1997; 1339(1):14-22. doi:10.1016/S0167-4838(96) 00212-9
35. El-Say K M. *Drug Des Devel Ther.* 2016; 10:825-839. doi:10.2147/DDDT.S101900
36. Kim B K, Hwang S J, Park J B, Park H J. *J Microencapsul.* 2002; 19(6):811-822. http://www.ncbi.nlm.nih.gov/pubmed/12569029.
37. Haznedar S, Dortunc B. *Int J Pharm.* 2004; 269(1):131-140.
38. Hu K, McClements D J. *Food Res Int.* 2014; 64:329-335. doi: 10.1016/j.foodres.2014.07.004
39. Nishiura H, Sugimoto K, Akiyama K, et al. *J Nanomed Nanotechnol.* 2013; 04(01):1-7. doi:10.4172/2157-7439.1000155
40. Wiśniewska M, Ostolska I, Szewczuk-Karpisz K, et al. *J Nanopart Res.* 2015; 17(1):12. doi:10.1007/s11051-014-2831-2
41. Mujtaba A, Ali M, Kohli K. *Chem Eng Res Des.* 2014; 92(1):156-165. doi: 10.1016/j.cherd.2013.05.032
42. Abdelwahed W, Degobert G, Stainmesse S, Fessi H. *Adv Drug Deliv Rev.* 2006; 58(15):1688-1713. doi:10.1016/j.addr.2006.09.017
43. Chen D B, Yang T Z, Lu W L, Zhang Q. *Chem Pharm Bull (Tokyo).* 2001; 49(11):1444-1447. doi:10.1248/cpb.49.1444
44. Fernández-Carneado J, Kogan M J, Castel S, Giralt E. Angew Chemie—Int Ed. 2004; 43(14):1811-1814. doi: 10.1002/anie.200352540

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGMENT

This project was funded by the Deanship of Scientific Research (DSR) at King Abdulaziz University, Jeddah, under grant no. (RG-3-166-40). The authors, therefore, acknowledge with thanks DSR for technical and financial support.

We claim:

1. A plurality of nanoparticles, each of said nanoparticles comprising dapoxetine, zein and alpha-lipoic acid (ALA), wherein the dapoxetine is present in a weight percentage of 3 to 35; the zein is present in a weight percentage of 50 to 70, and the ALA is present in a weight percentage of 3 to 10.

2. The nanoparticles of claim 1, wherein the nanoparticles range in size from 145 to 210 nm.

3. The nanoparticles of claim 1, wherein the nanoparticles have a zeta potential of 20 to 25 mvolts.

4. A pharmaceutical composition comprising the nanoparticles of claim 1.

5. A method of treating or preventing premature ejaculation (PE) in a subject in need thereof, comprising administering to the subject a therapeutically effective dose of the pharmaceutical composition of claim 4.

6. The method of claim 5, wherein the therapeutically effective dose is less than 30 mg.

7. A method of making nanoparticles as claimed in claim 1 comprising dapoxetine, zein and alpha-lipoic acid (ALA), comprising combining a DPX-zein-ALA organic solution with an aqueous polyvinyl alcohol (PVA) solution to yield a colloidal dispersion of the nanoparticles.

8. The method of claim 7, wherein the organic solution is a methanolic solution.

9. The method of claim 8, further comprising steps of
removing organic solvent from the colloidal dispersion; and
removing water from the colloidal dispersion.

10. The method of claim 9, wherein the step of removing water is performed by lyophilization.

11. The method of claim 8, further comprising one or more steps of washing, centrifugation and/or dialysis.

12. The method of claim 8, wherein the step of combining is performed by stirring at 1000_rpm or greater.

13. A plurality of nanoparticles, each of said nanoparticles comprising dapoxetine, zein and alpha-lipoic acid (ALA), wherein the nanoparticles have a zeta potential of 20 to 25 mvolts.

\* \* \* \* \*